United States Patent
Vasiev et al.

(10) Patent No.: US 12,427,265 B1
(45) Date of Patent: Sep. 30, 2025

(54) HOLD ASSISTANCE DEVICE

(71) Applicant: Genzyme Corporation, Cambridge, MA (US)

(72) Inventors: Iskandar Vasiev, Melbourn (GB); Kiara May-Leen Taylor, Cambridge (GB); Adam Christopher Nightingale, Cambridge (GB); Tom Alan Oakley, Cambridge (GB); Joel John Williams, Cambridge (GB); Matthew Christopher Latham, Cambridge (GB); Haiming Wu, Cambridge, MA (US)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 18/984,923

(22) Filed: Dec. 17, 2024

(51) Int. Cl.
*A61M 5/32* (2006.01)

(52) U.S. Cl.
CPC ... *A61M 5/3204* (2013.01); *A61M 2205/0288* (2013.01)

(58) Field of Classification Search
CPC ........ A61M 5/3204; A61M 2205/0288; A61M 2005/31588; A61M 2005/2073
See application file for complete search history.

(56) References Cited

U.S. PATENT DOCUMENTS

| | | | |
|---|---|---|---|
| 2018/0169337 A1* | 6/2018 | Paschal | A61M 5/20 |
| 2019/0224414 A1* | 7/2019 | Schabbach | A61M 5/2033 |

FOREIGN PATENT DOCUMENTS

WO    WO 2017/016961 A1    2/2017

OTHER PUBLICATIONS

Needle-based injection systems for medical use requirements and test methods, Part 1: Needle injection systems, ISO 11608 1:2014(E), Third Edition, Switzerland, ISO, Dec. 15, 2014, pp. 1-13.

\* cited by examiner

*Primary Examiner* — Kevin C Sirmons
*Assistant Examiner* — Hamza A Darb
(74) *Attorney, Agent, or Firm* — Fish & Richardson P.C.

(57) ABSTRACT

A hold assistance device for use with a medicament delivery device is described. The hold assistance device includes: a first support configured to be fixedly coupled to a main body of a medicament delivery device, wherein the first support comprises a first attraction component; and a second support moveable relative to the first support between an initial position and a hold position and configured to be fixedly coupled to a needle cover of the medicament delivery device, wherein the second support includes a second attraction component, and wherein at least one of the first attraction component and the second attraction component is a magnet, and the other of the first attraction component and the second attraction component is a magnet or a ferromagnetic material; and wherein movement of the second support towards the hold position moves the second attraction component towards the first attraction component.

13 Claims, 9 Drawing Sheets

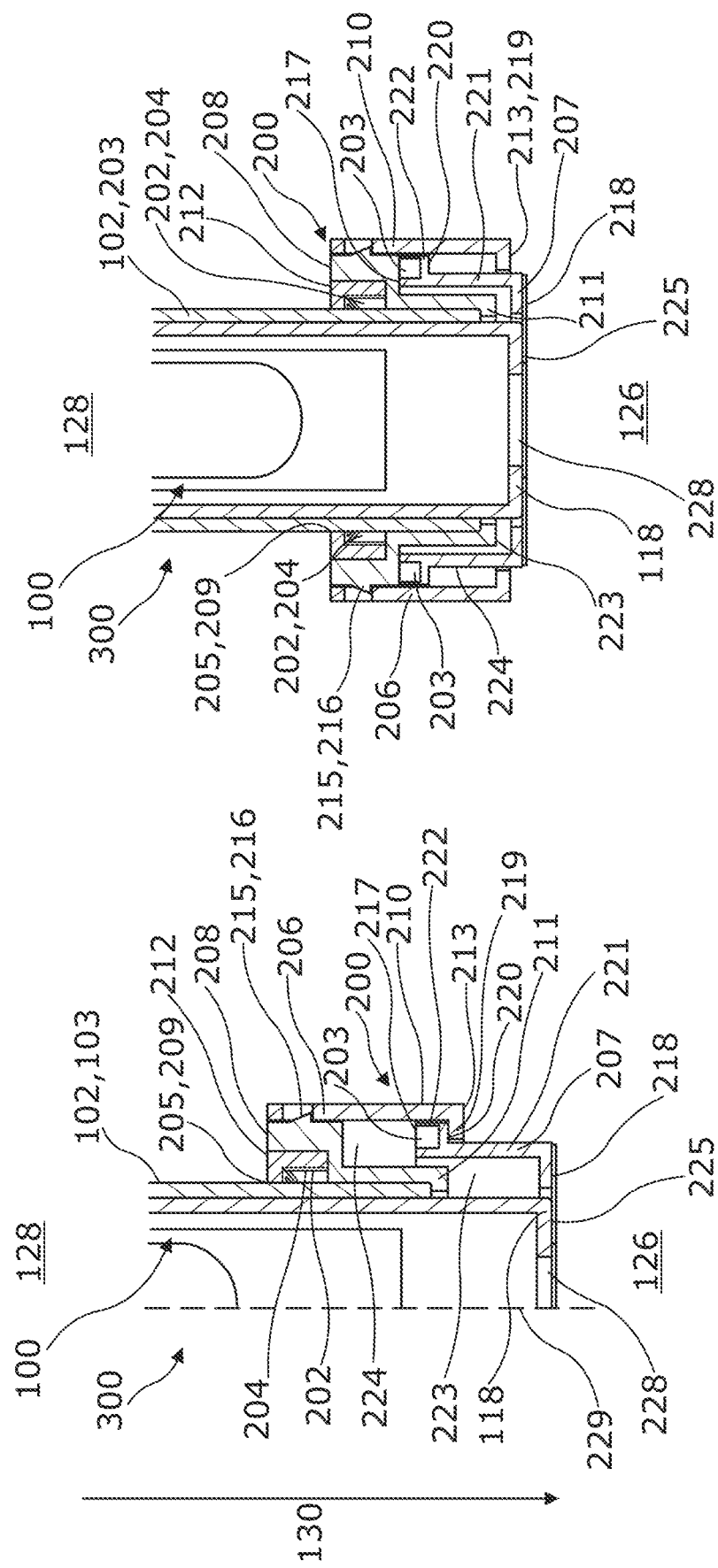

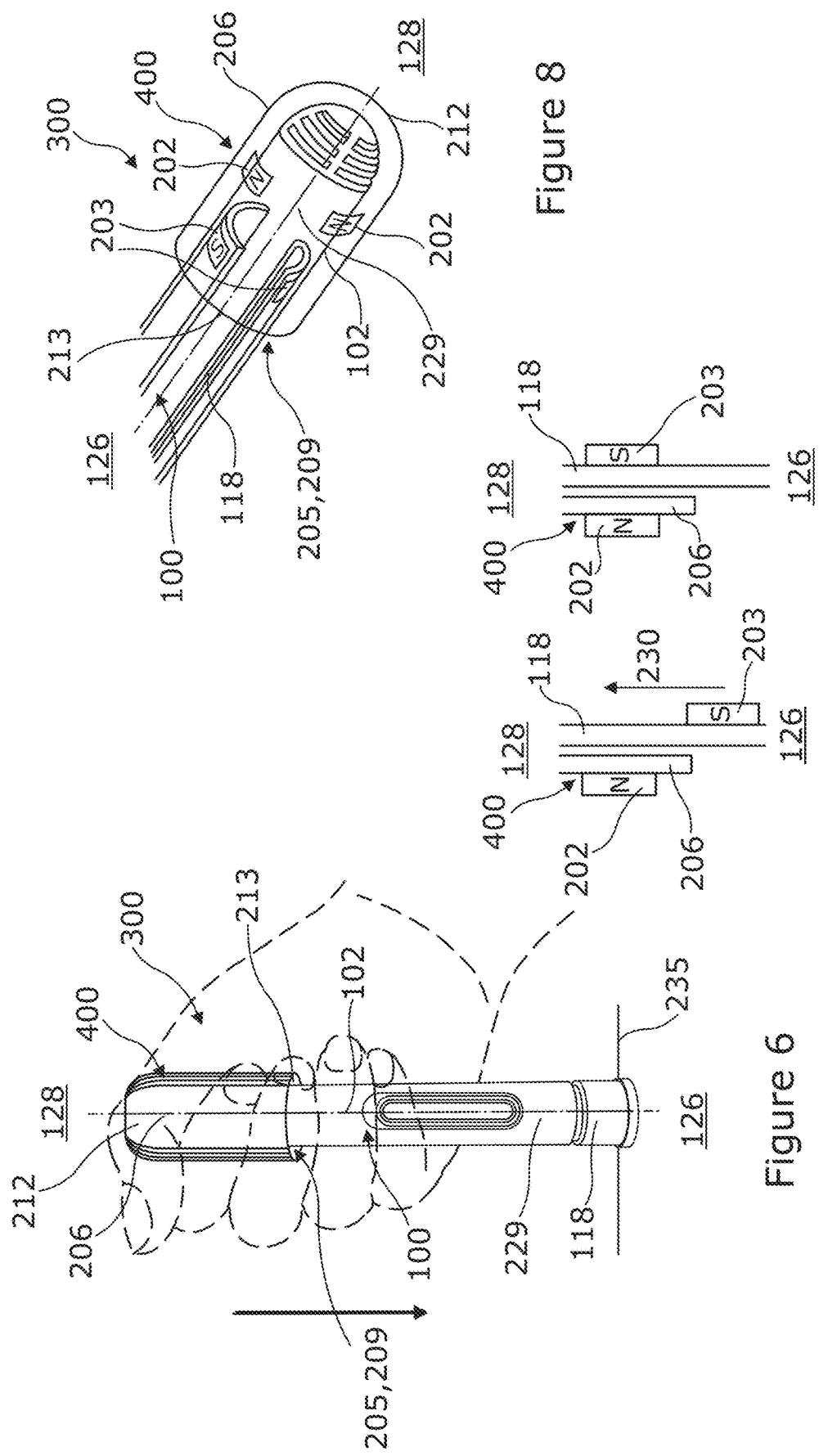

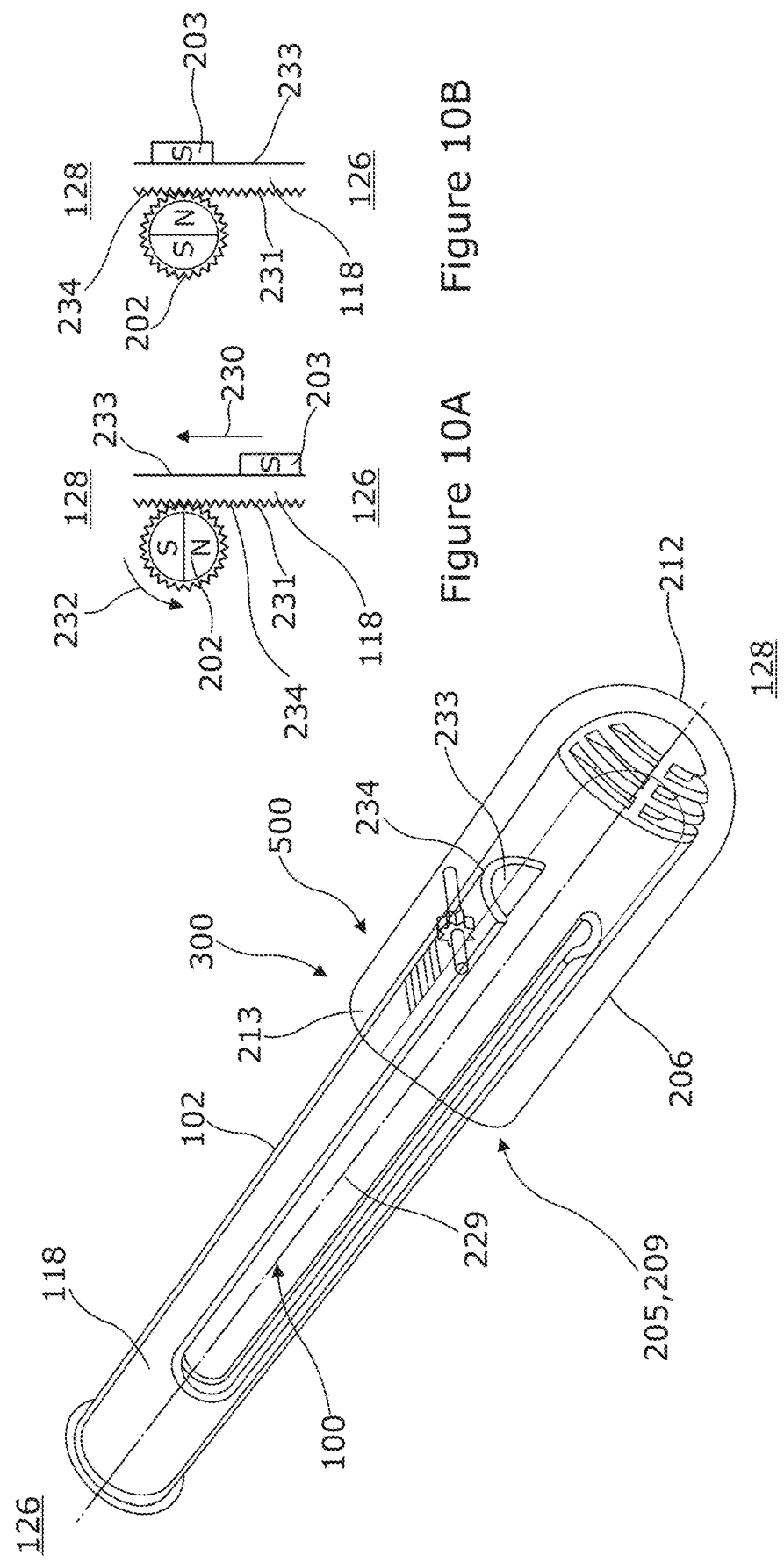

HOLD ASSISTANCE DEVICE

TECHNICAL FIELD

The present disclosure relates to a hold assistance device for a medicament delivery device, a medicament delivery system comprising a hold assistance device, a method of operating a medicament delivery system, and a method of assembling a medicament delivery system.

BACKGROUND

Medicament delivery devices are used to deliver a range of medicaments. In some devices, the device must be held in a holding position at an injection site to ensure that the correct dose of medicament is dispensed from the device, before removing the device from the injection site. It may be difficult to hold the device in the holding position whilst the medicament is dispensed. This may result in pain, discomfort, a wet injection site, early device removal and/or partial delivery of the medicament. Administering an injection involves various risks and challenges, encompassing both mental and physical aspects.

SUMMARY

The present disclosure provides a hold assistance device for a medicament delivery device.

A first aspect of this disclosure provides a hold assistance device for use with a medicament delivery device, the hold assistance device comprising: a first support configured to be fixedly coupled to a main body of a medicament delivery device, wherein the first support comprises a first attraction component; and a second support, moveable relative to the first support between an initial position and a hold position, and configured to be fixedly coupled to a needle cover of a medicament delivery device, and wherein at least one of the first attraction component and the second attraction component is a magnet, and the other of the first attraction component and the second attraction component is a magnet or a ferromagnetic material; and wherein movement of the second support towards the hold position moves the second attraction component towards the first attraction component, increasing magnetic attraction between the first attraction component and the second attraction component to generate a magnetic attraction force, wherein when the second support is in the hold position, the magnetic attraction force is configured to reduce a hold force required to keep the needle cover of the medicament delivery device in the retracted position by resisting movement of the needle cover towards the extended position.

The second support may comprise a second cavity for receiving a portion of the first support, when the second support is in the hold position.

The first support may comprise a first cavity for receiving a portion of the second support, when the second support is in the hold position.

The second support may comprise a proximal cylindrical portion and a distal cylindrical portion, wherein the distal cylindrical portion may have a diameter greater than the proximal cylindrical portion.

The second support may comprise a blocking portion for engagement with a needle cover of a medicament delivery device, wherein the blocking portion is configured to block movement of the needle cover in a distal direction.

The blocking portion may be disposed at a distal most end of the second support, and may extend at least partially towards a central axis of the hold assistance device, wherein the blocking portion may comprise an aperture in the centre to enable a needle to protrude during medicament delivery.

The hold assistance device may comprise a receiving volume for receiving a medicament delivery device, wherein the blocking portion may be a protrusion that extends into the receiving volume, at least partially towards a central axis of the hold assistance device, to engage with a needle cover of a medicament delivery device received in the receiving volume.

The hold assistance device may comprise one or more of the optional features recited above or below in relation to the other aspects of this disclosure.

A second aspect of this disclosure provides a hold assistance device for use with a medicament delivery device comprising a main body and a needle cover disposed within the main body and moveable between an extended position and a retracted position, the hold assistance device comprising: a first support configured to be fixedly coupled to the main body of the medicament delivery device, wherein the first support comprises a first attraction component for engagement with a second attraction component fixedly coupled to the needle cover of the medicament delivery device, wherein the first attraction component is a magnet or a ferromagnetic material; and wherein movement of the needle cover towards the retracted position moves the second attraction component towards the first attraction component of the hold assistance device, increasing magnetic attraction between the first attraction component and the second attraction component to generate a magnetic attraction force, wherein the magnetic attraction force of the hold assistance device is configured to reduce a hold force required to keep the needle cover of the medicament delivery device in the retracted position by resisting movement of the needle cover towards the extended position.

The first support may comprise an attachment mechanism for fixedly attaching the hold assistance device to the medicament delivery device.

The first support may comprise an adapter configured to house the attachment mechanism, and an outer housing surrounding the adapter, wherein the adapter may be adapted to suit different types of medicament delivery device without changing the dimensions of the outer housing.

The attachment mechanism may be a mechanical gripping means such as a retention clip, a pressing, a series of teeth, a latch and/or a star washer.

The attachment mechanism may be configured to act as the first attraction component.

The first attraction component may be a ferromagnetic material and the second attraction component may be a magnet.

The first attraction component may be a magnet and the second attraction component may be a magnet.

The first attraction component and/or the second attraction component may be arranged in a hoop configuration.

The magnet may be a permanent magnet.

The magnet may be a programmable magnet.

The hold assistance device may comprise a secondary hold component moveable between a rest position in which the secondary hold component may be configured to be disengaged from the first support, and an activated position in which the secondary hold component may be configured to be engaged with the first support, wherein the secondary hold component may be configured to be in the activated position when the second attraction component and the first attraction component are engaged to generate the magnetic attraction force, and the secondary hold component may be configured to disengage from the activated position, when the magnetic attraction force is released.

The first attraction component may be arranged in a first plane, and the second attraction component may be arranged in a second plane, and may be axially moveable along a path in the second plane, wherein the first plane may be generally parallel to the second plane, such that the second attraction component may be configured to slide linearly into engagement with the first attraction component.

The first path and the second path may be parallel with a central axis of the hold assistance device.

The first attraction component may be rotationally moveable along a first path, and the second attraction component may be linearly moveable along a second path, wherein the first path may be substantially parallel to the second path, such that the first attraction may be configured to rotate into engagement with the second attraction component.

The first attraction component may be a toothed gear rotatable along a rack as the second attraction component is moved towards the first attraction component.

The hold assistance device may comprise one or more of the optional features recited above or below in relation to the other aspects of this disclosure.

A third aspect of this disclosure provides a medicament delivery system comprising a hold assistance device and a medicament delivery device, wherein the medicament delivery device comprises: a main body arranged to receive a medicament cartridge; a needle for delivery of medicament from the medicament cartridge; a needle cover moveable relative to the main body between an extended position, in which the needle cover covers the needle, and a retracted position for dispensing medicament from the medicament delivery device, wherein in the retracted position the needle protrudes from a distal end of the needle cover; and wherein the first support comprising the first attraction component is configured to be coupled to the main body, and the second attraction component is configured to be coupled to the needle cover.

The medicament delivery system may further comprise a control spring to bias the needle cover away from the retracted position, wherein the magnetic attraction provided by the first attraction component and the second attraction component may counteract a force of the control spring moving the needle cover away from the retracted position.

The needle cover biasing member may comprise one or more springs, for example a compression spring.

The needle cover biasing member may comprise a spring, and when the first attraction component is engaged with the second attraction component, the spring may be configured to be compressed.

The needle cover biasing member may comprise a spring, and when the first attraction component is engaged with the second attraction component, the spring may be configured to be in an uncompressed state.

The hold assistance device may be removably couplable to the medicament delivery device.

The needle cover biasing member may be configured to exert a biasing force to bias the needle cover axially in the distal direction towards the extended position. The biasing force may be between approximately 10N and 15N.

The hold assistance device may be generally cylindrical. The hold assistance device may be generally annular.

The hold assistance device may be configured to be arranged at a distal end of a medicament delivery device.

The medicament delivery system may comprise a medicament cartridge containing medicament.

The medicament delivery system may comprise one or more of the optional features recited above or below in relation to the other aspects of this disclosure.

A fourth aspect of this disclosure provides a method of operating a medicament delivery system comprising: moving a needle cover relative to a main body of the medicament delivery device from an extended position, in which the needle cover covers the needle, towards a retracted position for dispensing medicament, in which the needle protrudes from a distal end of the needle cover; moving the second attraction component coupled to the needle cover towards the first attraction component coupled to the main body to increase magnetic attraction between the first attraction component and the second attraction component, to generate a magnetic attraction force; reducing a hold force required to keep the needle cover of the medicament delivery device in the retracted position, whereby the magnetic attraction force resists movement of the needle cover towards the extended position.

Moving the needle cover from the extended position to the retracted position may cause the needle cover to retract inside the main body such that the needle is exposed, which may be to place the medicament delivery device in a state ready for medicament to be delivered from the needle to an injection site of a patient.

Moving the needle cover from the extended position to the retracted position may comprise placing the medicament delivery device against a surface, for example against the skin of a patient at an injection site and applying a force in the distal direction towards the surface, thus pushing the needle cover against the surface and causing it to be pushed inside the main body to retract thereinside.

Moving the second attraction component coupled to the needle cover towards the first attraction component coupled to the main body to increase magnetic attraction between the first attraction component and the second attraction component, to generate a magnetic attraction force may be configured to occur simultaneously with the step of moving the needle cover from the extended position to the retracted position.

The method may further comprise a step of holding the medicament delivery device for a required duration of time at an injection site of a patient. For example, the method may comprise holding the medicament delivery device at an injection site for the amount of time required for completion of delivery of a medicament from the needle to be complete.

Holding the medicament delivery device for a required duration of time at an injection site of a patient may occur after the step of moving the second attraction component coupled to the needle cover towards the first attraction component coupled to the main body to increase magnetic attraction between the first attraction component and the second attraction component, to generate a magnetic attraction force.

The magnetic attraction force acting on the needle cover may be released by removing a user hold force acting on the medicament delivery device, such that the needle cover moves towards its extended position and the second attraction component is moved out of engagement with the first attraction component.

The magnetic attraction force acting on the needle cover may be released by moving the medicament delivery device away from a surface, for example away from the skin of a patient at an injection site.

The method of operating a medicament delivery system may comprise one or more of the optional features recited above in relation to the other aspects of this disclosure.

A fifth aspect of this disclosure provides a method of assembling a medicament delivery system comprising coupling a hold assistance device to a medicament delivery device to form a medicament delivery system.

The method of assembling a medicament delivery system may comprise one or more of the optional features recited above in relation to the other aspects of this disclosure.

The details of one or more embodiments of the subject matter of this specification are set forth in the accompanying drawings and the description below. Other features, aspects, and advantages of the subject matter will become apparent from the description, the drawings, and the claims.

BRIEF DESCRIPTION OF THE DRAWINGS

Embodiments will now be described, by way of example only, with reference to the accompanying drawings, in which:

FIG. 4 shows a schematic cross section of the medicament delivery system of FIG. 2, when a needle cover is in an extended position;

FIG. 5 shows a schematic cross section of the medicament delivery system of FIG. 2, when a needle cover is in a retracted position;

FIG. 6 shows a schematic view of a medicament delivery system including a hold assistance device disposed at a proximal end of a medicament delivery device;

FIG. 7A shows a schematic example of a first and second attraction component of the medicament delivery system of FIG. 6 in a disengaged position;

FIG. 7B shows a schematic example of a first and second attraction component of the medicament delivery system of FIG. 6 in an engaged position;

FIG. 8 shows a schematic view of the medicament delivery system of FIG. 6, with parts of the medicament delivery system shown transparent so that the first and second attraction components are visible;

FIG. 9 shows a schematic view of another example of the medicament delivery system of FIG. 6, with parts of the medicament delivery system shown transparent so that the first and second attraction components are visible;

FIG. 10A shows a schematic example of a first and second attraction component of the medicament delivery system of FIG. 9 in a disengaged position;

FIG. 10B shows a schematic example of a first and second attraction component of the medicament delivery system of FIG. 9 in an engaged position;

DETAILED DESCRIPTION

Figure 1:
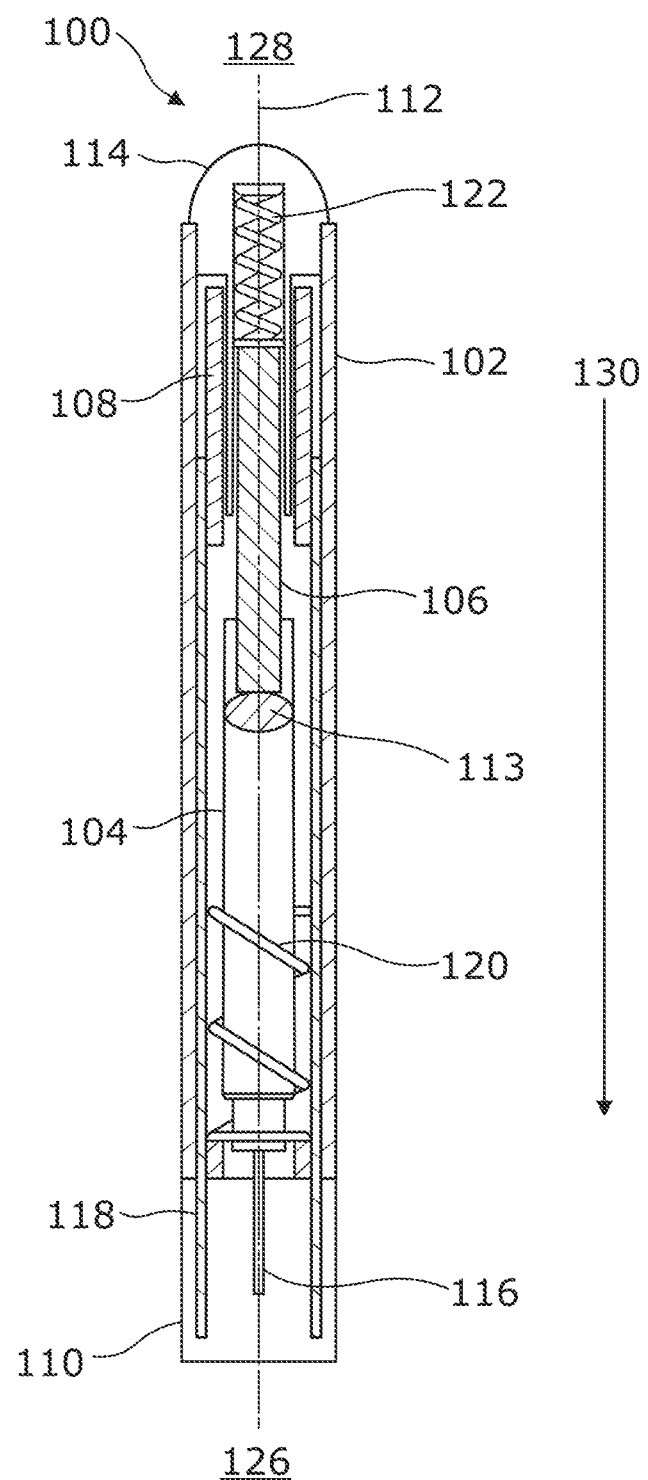
FIG. 1 shows a schematic cross section of a medicament delivery device.

A drug delivery device (also referred to as an injection device, or a medicament delivery device), as described herein, may be configured to inject a medicament into a subject such as a human or animal. For example, a delivery of the medicament could be sub-cutaneous, intra-muscular, or intravenous. Such a device could be operated by a user, who may or may not be the subject. In examples where the user is not the subject, the user may be a caregiver such as a nurse or physician. The device can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a subject's skin for a period of time (e.g., about 5, 15, 30, 60, or 120 minutes) to deliver a "large" volume of medicament (e.g., about 2 ml to about 10 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The delivery devices described herein can also include one or more automated functions. For example, one or more of a needle insertion, a medicament injection, or a needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may each be activated via an activation mechanism. Such an activation mechanism can include one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

Auto-injectors require user actions to commence medicament delivery. One of these actions may involve a user placing a needle cover (also referred to as a needle shroud or needle sleeve) against an injection site of a subject and applying an axial force to the device to cause the needle cover to retract into the housing of the device. As the needle cover retracts into the housing, the needle of the device extends beyond the needle cover and penetrates the injection site of the subject (e.g. the subject's skin). Medicament delivery may be automatically initiated in response to the retraction of the needle cover or in response to another action by the user, for example the user pressing a button on the device. Once medicament delivery has been initiated, a medicament delivery mechanism will cause medicament contained within the device to be injected into the subject via the needle. The user should hold the device steady with respect to the injection site during the course of medicament delivery to ensure the needle remains steady within the subject. This is to minimise pain and/or discomfort for the subject, and to prevent a wet injection site, an early device removal and/or a partial medicament delivery.

After the device is removed from the injection site, many autoinjectors cover the needle with the needle cover/needle shroud, which is extended out of the device by a control spring. During activation of the device and while holding the device steady during medicament delivery, the user must counteract the biasing force applied by the control spring to the needle cover. This can be referred to as the hold force. However, some users such as those with impaired dexterity may find it difficult to hold the device steady for a relatively long period of time during medicament delivery. It may be beneficial to provide a device which is easier to handle during medicament delivery.

FIG. 1 shows a schematic example of a cross section of a medicament delivery device 100 (hereinafter referred to as an injection device) according to one or more aspects of the present disclosure. The injection device 100 is configured to inject a medicament into a subject. The injection device 100 comprises an outer casing 102 (also referred to as a housing or injection device body) that encloses a reservoir 104, a plunger 106 and a rotatable collar 108. The reservoir 104 typically contains the medicament to be injected, and may, for example, be in the form of a syringe. The injection device 100 can also include a cap assembly 110 that can be detachably mounted to the outer casing 102. A user typically removes cap 110 from the outer casing 102 before device 100 is operated.

As shown in FIG. 1, the outer casing 102 is substantially cylindrical and has a substantially constant diameter along the longitudinal axis of the device 100. The injection device 100 has a distal region 126 and a proximal region 128. The term "distal" refers to a location that is relatively closer to a site of injection, and the term "proximal" refers to a location that is relatively further away from the injection site.

The outer casing 102 is closed at a proximal end by a rear casing 114. A needle 116 and a retractable needle cover 118 (also referred to as a "needle sleeve" or "needle cover") extend from a distal end of the outer casing 102. The retractable needle cover 118 is biased axially in the distal direction of the injection device 100, for example using a control spring 120. The needle cover 118 is coupled to the outer casing 102 to permit axial movement of needle cover 118 relative to the outer casing 102. For example, the cover 118 can move in a longitudinal direction parallel to longitudinal axis 112. Specifically, movement of cover 118 in a proximal direction relative to the outer casing 102 can cause a needle 116 to extend from distal region of the outer casing 102, and outside a distal end of the cover 118.

The plunger 106 is biased towards the distal end of the injection device 100 by a biasing means, for example comprising a drive spring 122. The plunger 106 is retained in an initial position by a combination of the rear casing 114 and the collar 108, preventing the biasing means from displacing the plunger 106 in the distal direction. Activation of the injection device 100 causes the collar 108 to rotate, which releases the plunger 106. Once released, the biasing means causes the plunger 106 to move in the distal direction (i.e., towards the needle 116 end of the injection device 100). The plunger 106 contacts a stopper 113 in the reservoir 104, displacing the stopper 113 in the distal direction and causing medicament stored in the reservoir 104 to be expelled from the injection device 100 via the needle 116.

Activation of the injection device 100 can occur via several mechanisms. For example, the needle 116 may be fixedly located relative to the outer casing 102 and initially be located within an extended needle cover 118. Proximal movement of the needle cover 118 by placing a distal end of the cover 118 against an injection site of the subject and moving the outer casing 102 in a distal direction will uncover the distal end of the needle 116. Such relative movement allows the distal end of the needle 116 to extend into the injection site. Such insertion is referred to as a "manual" insertion as the needle 116 is manually inserted via the user's manual movement of the outer casing 102 relative to cover 118. Retraction of the cover 118 into the outer casing 102 causes the collar 108 to rotate, thereby releasing the plunger 106.

Another form of activation is "automated", whereby the needle 116 moves relative to outer casing 102. Such insertion can be triggered by movement of the cover 118 and/or by another form of activation, such as a user actuation of a button (not shown) of the injection device 100.

Typically, the user presses the needle cover 118 against an injection site to push the needle cover 118 at least partially into the outer casing 102. The exposed needle 116 is pushed into the injection site of the subject. In a holding position, a medicament is automatically dispensed from the needle 116 via an automated mechanism. The user typically holds the needle cover 118 in the holding position for a predetermined period of time to ensure that the correct dose of medicament is dispensed from the device 100 before removing the device 100 from the injection site.

The spring biasing force 130 from the control spring 120 against which the user must apply a force to move the needle cover 118 is one component of an "activation force" of the device 100.

The activation force refers to the force or force profile that the user must exert on the device 100 to move the needle cover 118 from the extended position shown in FIG. 1 to a retracted position within the outer casing 102 for medicament delivery. If this force or force profile is not well balanced, it can lead to difficulty in activating the device 100 for some users, or increase the pain or anxiety associated with using the device 100.

Following the injection, the needle 116 can be retracted within the cover 118. Retraction can occur when the cover 118 moves distally under the biasing of the control spring 120 as a user removes the device 100 from the injection site of the subject. Once a distal end of the cover 118 has moved past a distal end of the needle 116 such that the needle 116 is covered, the cover 118 may be locked in its extended position to prevent any (substantial) proximal movement of the cover 118 relative to the outer casing 102 (i.e., preventing any movement of the cover 118 that would uncover the needle 116). The cover 118 may be locked by a needle cover non-return element (not shown), such as a catch.

FIGS. 2 to 5 show an example of a medicament delivery system 300 comprising a medicament delivery device 100 and a hold assistance device 200. For brevity, only a portion of the main body 102 and the needle cover 118 of the medicament delivery device 100 is shown in FIGS. 2 to 5.

The hold assistance device 200 is for use with the medicament delivery device 100 to reduce the amount of hold force required by a user when dispensing medicament from the medicament delivery device 100. The medicament delivery device 100 may be substantially similar or identical to the injection device 100 shown in FIG. 1 and described above, and similar features have been given the same reference numerals.

The hold assistance device 200 has a receiving volume 205 for receiving the medicament delivery device 100. The medicament delivery device 100 and the hold assistance device 200 are configured to be coupled together to form the medicament delivery system 300. As such, the hold assistance device 200 is arranged to surround at least a portion of the medicament delivery device 100. Furthermore, the hold assistance device 200 may configured to be removeable from the medicament delivery device 100, such that the hold assistance device may be reuseable and/or disposable.

The hold assistance device 200 may be assembled together with the medicament delivery device 100 to form the medicament delivery system 300. Alternatively, the hold assistance device 200 and the medicament delivery device 100 may be supplied separately, and then assembled by the user or another person, to form the medicament delivery system 300. It is also envisaged that the hold assistance device 200 may be retrofitted to existing medicament delivery devices, and/or may be used with medicament delivery devices other than that shown in the example in FIG. 1.

As mentioned above with reference to FIG. 1, the needle cover 118 is extended out of the device by a biasing member 120, for example by a control spring (not shown). The biasing member 120 is arranged to bias the needle cover 118 towards an extended position, in which the needle cover 118 protrudes from a distal end 126 of the main body 102 to cover the needle 116. The needle cover 118 is moveable relative to the main body 102 between an extended position, in which the needle cover 118 covers the needle 116, and a retracted position for dispensing medicament from the medicament delivery device 100. In the retracted position the needle 116 protrudes from a distal end 126 of the needle cover 118.

To move the needle cover 118 to the retracted position, and while holding the medicament delivery device 100 steady during medicament delivery, the user must counteract a biasing force 130 applied by the biasing member 120 to the needle cover 118.

The needle cover biasing member 120, for example a spring, is arranged to bias the needle cover 118 towards an extended position (see FIGS. 2, 3 and 4 for example) in which the needle cover 118 protrudes from the main body 102 at a distal end 126 of the medicament delivery device 100 such that the needle 116 is covered by the needle cover 118. For example, when the needle cover 118 is in the extended position, the needle cover biasing member 120 may for example be a compression spring in its natural extended, uncompressed state. Thus, when the needle cover 118 is in a retracted position (see FIG. 5) in which the needle cover 118 is retracted in a proximal position relative to the extended position such that the needle cover 118 is retracted inside the main body 102 and the needle 116 is not covered by the needle cover 118, this goes against the biasing action of the needle cover biasing member 120. For example, where the needle cover biasing member 120 is a compression spring, this causes the needle cover biasing member 120 to be compressed.

Figure 3:
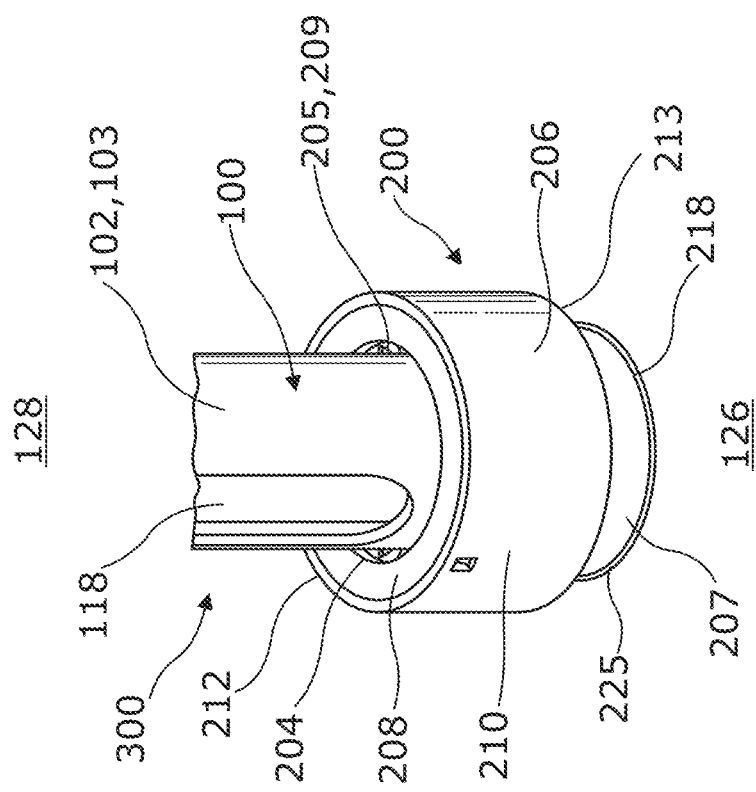
FIG. 3 shows a schematic view of the medicament delivery system of FIG. 2, showing a proximal end of the hold assistance device.
Figure 2:
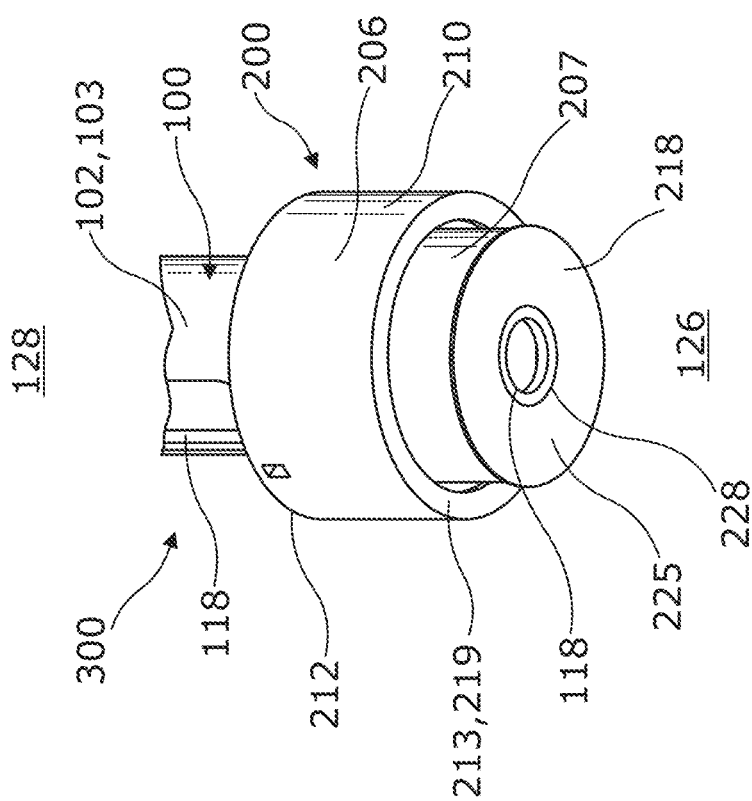
FIG. 2 shows a schematic view of a medicament delivery system including a hold assistance device, showing the distal end of the hold assistance device.

A biasing force 130, for example a spring force 130, which acts in the direction shown in FIGS. 1 and 4 for example by the arrow 130, will inherently bias the needle cover 118 back towards the extended position shown in FIGS. 2, 3 and 4. That is, because moving the needle cover 118 from the extended position to the retracted position goes against the action of the needle cover biasing member 120, for example by compressing a spring, the needle cover biasing member 120 hence biases the needle cover 118 axially in the distal direction 126 towards the extended position. Thus, once the needle cover 118 has been placed into the retracted position, in order to maintain the needle cover 118 in the retracted position so that the needle 116 remains uncovered and can be used for the required duration of time to deliver medicament to a user, force is required by the user in order to counteract the biasing force 130, to prevent the needle cover 118 from extending distally.

The hold assistance device 200 acts to counteract the biasing force 130, by using magnetic attraction to offset the user hold force of the medicament delivery device 100.

The hold assistance device 200 reduces the amount of force required from a user to hold the medicament delivery device 100 in a medicament delivery state in which the needle cover 118 is retracted, i.e. it reduces the amount of force which needs to be applied by the user to resist the biasing force 130. The hold assistance device 200 does this by holding the needle cover 118 in place with a magnetic attraction force in order to hold the needle cover 118 in the retracted position, to prevent it from inadvertently moving towards the distal end 126 of the medicament delivery device 100, until medicament delivery is complete, at which point the needle cover 118 may be allowed to expand again under the action of the needle cover biasing member 120. In other words, the hold assistance device 200 provides a magnetic attraction force which can offset the user hold force of a medicament delivery device.

The hold assistance device 200 has a first support 206 coupled to the main body 102 by an attachment mechanism 204. The first support 206 is configured to remain fixed, i.e. stationary, relative to the main body 102—i.e. the first support 206 is not movable relative to the main body 102 when the hold assistance device 200 is coupled to the medicament delivery device 100. The connection between the first support 206 and the main body 102 may be configured to be removable, such that the hold assistance device 200 may be removed from the medicament delivery device 100.

The attachment mechanism 204 may be a mechanical gripping means, for example a retention clip, a pressing, a series of teeth, a latch or a star washer and it may be metal, plastic or an alternative suitable material. The attachment mechanism 204 is configured to latch on to the medicament delivery device 100 to lock the main body 102 of the medicament delivery device 100 to the first support 206, in such a way that axial movement of the main body 102 also axially moves the first support 206. The attachment mechanism 204 also resolves any axial force from pushing the needle cover 118 into the main body 102. In the example shown in FIGS. 2 to 5, the attachment mechanism 204 is arranged to engage with an external face of a side wall 103 of the main body 102.

As illustrated best in FIG. 4, the first support 206 comprises a first attraction component 202. The first attraction component 202 is a magnet or a ferromagnetic material. The first attraction component 202 is embedded into or coupled in to the first support 206 towards a proximal end 212 of the first support 206. As illustrated in FIG. 4, the attachment mechanism 204 is a metal gripping ring made of a ferromagnetic material and therefore is able to act as the first attraction component 202. This assists in reducing the number of parts and also the weight of the hold assistance device 200.

The first support 206 has a receiving volume 209 for receiving the medicament delivery device 100. The first support 206 further comprises an adapter 208 disposed around the receiving volume 209, for housing the attachment mechanism 204 and contacting the main body 102 in use. The adapter 208 may have a secondary latch or retention clip 211 (shown best in FIG. 4) to further assist in resisting axial movement of the adapter 208 relative to the main body 102. The secondary latch 211 latches on to a distal most end of the main body 102. The secondary latch 211 has a flange which extends internally towards a central axis 229 of the first support 206 to engage with the main body 102. However, the secondary latch 211 does not extend in such a manner that it engages with the needle sleeve 118.

The first support 206 comprises a proximal end 212 and a distal end 213. Hereinafter, movement in a direction away from the distal end 213 and towards the proximal end 212 may be referred to as movement in a proximal direction, and movement in a direction away from the proximal end 212 and towards the distal end 213 may be referred to as movement in a distal direction. The first support 206 is generally cylindrical in shape and extends around the entire circumference of the main body 102. The first support 206 may be open at its proximal end such that the adapter 208 is visible, so the user assembling the medicament delivery system 300 by coupling the attachment mechanism 204 to the main body 102 can visually identify that the two components are safely connected.

The first support 206 has an outer housing 210 coupled to the adapter 208, for engagement with a second support 207 of the hold assistance device 200. The outer housing 210 comprises a connection portion 219 extending internally towards a central axis 229 of the first support 206 for engagement with a receiving portion 220 of the second support 207.

The adapter 208 is connected to the outer housing 210 by a press fit connection, an adhesive, or a mechanical connection means such as shown best in FIG. 4. As illustrated in FIG. 4, at least one of the adapter 208 and the outer housing 210 comprises a protrusion 215 for engagement with a notch 216 in the other of the adapter 208 and the outer housing 210. The outer housing 210 is generally cylindrical in shape and generally circumferentially continuous. However, it can be envisaged that the outer housing 210 extends around a smaller portion of the circumference of the main body 102, for example, if the outer housing 210 comprises a set of arms (not shown) to hold the adapter 208 in place. In some embodiments (not shown) the adapter 208 and the outer housing 210 are formed as a single component. In other embodiments, the adapter 208 is removeable and replaceable, such that it can be adapted to suit the type of medicament delivery device 100 the hold assistance device 200 is configured to be used with, whilst reusing the same first and second support 206, 207.

The hold assistance device 200 has a second support 207 having a proximal end 217 and a distal end 218. The second support 207 is configured to be coupled to the needle cover 118 of a medicament delivery device 100 at its distal end 218. The second support 207 is coupled to the first support 206 at its proximal end 217 and is moveable relative to the first support 206 between an initial position as shown in FIGS. 2 to 4 and a hold position as shown in FIG. 5. In the initial position, the second support 207 protrudes from the first support 206 such that the second support 207 is configured to cover a needle cover 118 of a medicament delivery device 100 when the needle cover 118 is in the extended position. In the hold position, the second support 207 is moved towards the first support 206, and is retracted within the first support 206, such that the second support 207 is configured to resist movement of the needle cover 118 of the medicament delivery device 100 from the retracted position, during the delivery of medicament.

The second support 207 comprises a second attraction component 203. The second attraction component 203 is a magnet or a ferromagnetic material. For example, if the first attraction component 202 is a magnet, the second attraction component 203 is a magnet or a ferromagnetic material. If the first attraction component 202 is a ferromagnetic material, then the second attraction component 203 is a magnet.

The first and second attraction components 202, 203 may be arranged in a hoop configuration such that they generally surround the receiving volume 205 of the hold assistance device 200. It is also envisaged that each of the first and second attraction components 202, 203 may be an array of individually arranged magnets disposed around the circumference of the receiving volume 205. For example, each may comprise between 1 and 10 magnets, between 2 and 8 magnets, or between 2 and 4 individually arranged magnets.

The second attraction component 203 is embedded into or coupled to the second support 207. The second attraction component 202 is disposed towards the proximal end 217 of the second support 207 to facilitate bringing the second attraction component 203 in close proximity of the first attraction component 202, to create the magnetic attraction force required to assist in holding the needle cover 118 in the retracted position. As shown in FIG. 4, the second attraction component 202 is disposed in the proximal most end 217 of the second support.

As mentioned above, the second support 207 comprises a receiving portion 220 for receiving the connecting portion 219 of the first support 206. The second support 207 is generally cylindrical in shape and is configured to extend around the circumference of the needle cover 118. The second support 207 comprises a distal cylindrical portion 221, and a proximal cylindrical portion 222. The distal cylindrical portion 221 has a different diameter to the proximal cylindrical portion 222, and in the example illustrated in FIG. 2, the distal cylindrical portion 221 has a larger diameter than the proximal cylindrical portion 222. There is a step provided between the distal cylindrical portion 221 and the proximal cylindrical portion 222 and this step can act as the receiving portion 220 for moveably coupling the second support 207 to the first support 206.

The second support 207 has an adapter cavity 223 (also referred to as a second cavity) for receiving the adapter 208 when the second support 207 is in the hold position. When the hold assistance device 200 is assembled with the medicament delivery device 100, the adapter cavity 223 is also configured to receive a portion of the main body 102 when the second support 207 is in the hold position and the needle cover 118 is in the retracted position. Between the adapter 208 and the outer housing 210 of the first support 206 there is a second support cavity 224 (also referred to as a first cavity) for receiving the second support 207 when the second support 207 is in the hold position, and when the hold assistance device 200 is assembled with the medicament delivery device 100, the needle cover 118 is in the retracted position.

When the second support 207 is in the hold position, a part of the main body 102 and the adapter 208 is disposed between the needle cover 118 and the distal cylindrical portion 222 of the second support 207 in the adapter cavity 223. Furthermore, when the second support 207 is in the hold position, the distal cylindrical portion 222 and the proximal cylindrical portion 221 are disposed between the adapter 208 and the outer housing 210, and between the main body 102 and the outer housing 210, within the second support cavity 224.

The second support 207 has a blocking portion 225 for engagement with the needle cover 118 when the hold assistance device 200 is assembled with the medicament delivery device 100, to prevent the needle cover 118 from moving from the retracted position until the first attraction component 202 has been disengaged from the second attraction component 203. In other words, the blocking portion 225 constrains distal axial motion of the needle cover 118. The blocking portion 225 is for example a flange, film, set of arms or moulded part of the second support 207 which the biasing force 130 of the biasing member 120 pushes against as the needle cover 118 is moved from the retracted position to the extended position. The blocking portion 225 may be a separate component coupled to the distal cylindrical portion 221 of the second support 207 or may be a continuous part of the second support 207. The blocking portion 225 is disposed towards a distal end 218 of the second support 207 and is configured to engage with a distal most end of the needle cover 118.

The blocking portion 225 is also configured to be pressed against a user's skin (or an injection surface) to move the needle cover 118 of the medicament delivery system 300 from the extended position to the retracted position, which can initiate the delivery of medicament from the medicament delivery device 100. The blocking portion 225 therefore comprises a smooth and comfortable surface to be pressed against a user's skin for the duration of medicament delivery. The blocking portion 225 may be made from a flexible, rigid or resilient material. Where the term 'resilient material' is used, this is intended to mean a material that is compressible as visible to the human eye, for example rubber and/or foam.

The blocking portion 225 further comprises an aperture 228 for the needle 116 to extend through during the delivery of medicament from the medicament delivery system 300. The thinner the blocking portion 225, the less impact the blocking portion 225 has on a penetration depth of the needle 116 when delivering medicament to a user. Therefore, it is advantageous to have a blocking portion 225 with a thickness of less than 1 mm, less than 0.5 mm, or less than 0.25 mm.

Alternatively, or additionally, the blocking portion 225 may comprise a mechanical interlock (not shown) between the needle cover 118 and the second support 207. For example, at least one of the needle cover 118 or the second support 207 comprises a protrusion, for engagement with a notch, chamfer or step in the other of the needle cover 118 and the second support 207. This mechanical interlock also enables the distal most end of the needle cover 118 to be clear, and therefore this type of blocking portion 225 has little or no impact on the penetration depth of the needle 116 when delivering medicament to a user. It can be envisaged that other known mechanical interlocks can be used between the needle cover 118 and the second support 207.

FIGS. 2 to 4 show the second support 207 in an initial position. When the hold assistance device 200 is coupled to a medicament delivery device 100, the second support 207 is configured to be in the initial position when the needle cover 118 is in the extended position, for example before delivery of a medicament from the needle 116 has occurred. In the initial position, the first attraction component 202 and the second attraction component 203 are spaced away from each other such that there is not enough magnetic attraction between the first attraction component 202 and the second attraction component 203 to noticeably affect the biasing force 130, such that the needle cover 118 is free to axially slide relative to the main body 102, for example to move in the distal direction under the action of the biasing force 130. In this configuration, the first attraction component 202 and the second attraction component 203 can be said to be disengaged from each other.

When the second support 207 is in the initial position, the second support 207 extends distally from the first support 206, and the receiving portion 220 of the second support 207 is coupled to, or in contact with, the outer housing connecting portion 219. Neither the adapter cavity 223, nor the second support cavity 224 have been entered by the adapter 208, and second support 206 respectively. The first attraction component 202 is at its maximum distance away from the second attraction component 203. The term 'extended position' is used for both a pre-use position, and an after-use position. However, it is envisaged that in an after use position (i.e. once the medicament has been delivered and the needle cover 118 extends to cover the needle 116) the needle cover 118 may extend further from the main body 102 in a distal direction, than in the pre-use position (i.e. before a user has pressed the injection device 100 on to a user's skin for the first time, also referred to as the initial position). The same may therefore be true of the second support 207 relative to the first support 206. For example, the second support 207 may extend further in a distal direction from the first support 206 in the after-use position, relative to the pre-use position. In such a case, in the pre-use or initial position the receiving portion 220 may not be in direct contact with the connecting portion 219, and the adapter cavity 223 and the second support cavity 224, are defined as per the initial or pre-use position.

FIG. 5 shows the medicament delivery system 300 in a subsequent stage of operation, in which the needle cover 118 has been retracted inside, or moved towards, the main body 102 into the retracted position, thus exposing the needle 116

(not shown), for example by pressing the medicament delivery device 100 against the skin of a user at an injection site 235. The position shown in the example of FIG. 5 may therefore correspond with the time at which a medicament is being injected into a patient.

When the needle cover 118 is in the retracted position, the second support 207 is in a hold position in which the first attraction component 202 and the second attraction component 203 have been brought towards each other to increase and/or generate a magnetic attraction between them. This magnetic attraction forms the magnetic attraction force configured to act against the biasing force 130 of the biasing member 120, resulting in a reduction of the hold force required from the user. As the medicament delivery system 300 is held against a user's skin, in combination with the assistance from the hold assistance device 200, the needle cover 118 is not able to extend under the force of the biasing member 120. In other words, the needle cover 118 is prevented from inadvertently moving distally into the extended position.

When the second support 207 is in the hold position, the second support 207 is arranged closer to the proximal end 212 of the first support 206 compared with when the second support 207 is in the initial position. That is, in order to move the second support 207 from the initial position to the hold position, the second support 207 is axially moved along the distal direction towards the proximal end 212 of the first support 206. Thus, distal axial movement of the second support 207 moves the second attraction component 203 towards the first attraction component, to engage the second attraction component 203 and the first attraction component 202. The biasing force 130 of the biasing member 120 still acts on the needle cover 118. However, the biasing force 130 causes the needle cover 118 to push against the blocking portion 225, and the blocking portion 225, which is part of the second support 206 held in the hold position by the magnetic attraction force, resists or prevents movement of the needle cover 118 into the extended position. When the medicament delivery system 300 is pressed against the user's skin, it further assists in preventing the needle cover 118 from moving into the extended position.

The second support 207 may be kept in the hold position for as long as is needed for the user of the medicament delivery system 300 to deliver medicament from the needle 116 of the medicament delivery device 100 to an injection site 235 of a user, in order to reduce the amount of force needed to be applied by the user to retain the needle cover 118 in the retracted position, in which the needle 116 is uncovered and can be used to deliver medicament. After delivery of the medicament from the needle 116 has been completed, the medicament delivery device 100 may be removed from the injection site 235 of the user, thus the hold force is no longer required. At this point, it may be desirable to recover the needle 116 with the needle cover 118 for safety and hygiene reasons, to help ensure safe removal and disposal of the medicament delivery device 100 from the injection site 235. Thus, it may be desired to bring the needle cover 118 back into the extended position in which it covers the needle 116. After medicament delivery, once in the extended position, the needle cover 118 may be locked in the extended position.

In order to allow the needle cover 118 to revert back into its extended position, under the action of the biasing force 130, the magnetic attraction force can be removed, or at least reduced in magnitude, in order to reduce or remove the resistance provided by the magnetic attraction force against the biasing force 130, such that the action of the needle cover biasing member 130 may be permitted to cause the needle cover 118 to move back into its extended position.

In order to reduce the magnitude of, or remove, the magnetic attraction force in order to permit the needle cover 118 to revert back into its extended position, the medicament delivery system 300 is removed from the user's skin. User applied pressure in a distal axial direction is therefore removed. The biasing force 130 pushes against the blocking portion 225, encouraging the second support 207 to be moved out of the hold position, and therefore the first attraction component 202 may be disengaged from the second attraction component 203, enabling the needle cover 118 to be extended under the force of the biasing member 120 without the biasing force 130 being resisted by the magnetic attraction force. Therefore, it is important that a residual force available in the biasing member 120 after offset by the magnetic attraction force is accounted for, is suitable for ensuring distal motion of the needle cover 118 into its extended position once medicament delivery has concluded.

The magnetic attraction force is strong when the first attraction component 202 and second attraction component 203 are in close proximity, but quickly diminishes as the first attraction component 202 is separated from the second attraction component 203, i.e. they are disengaged from one another. The force 130 of the biasing member 120 decreases as the biasing member 120 extends, therefore if the magnetic attraction force did not diminish quickly, there may be a risk of stalling of the needle cover 118 moving into the extended position after the delivery of medicament. As moving the needle cover 118 into the extended position after the delivery of medicament is a safety mechanism, it is important to avoid any delay or stall in the needle cover 118 moving back into the extended position.

FIGS. 6 to 8 show another example of a hold assistance device 400 and a medicament delivery system 300, wherein like reference numerals denote like elements. In the example shown, the second attraction component 203 is configured to slide towards the first attraction component 202 along a parallel axis to bring the second attraction component 203 into proximity of the first attraction component 202, and to increase the magnetic attraction to generate the magnetic attraction force to counteract the biasing force 130 of the biasing member 120.

The hold assistance device 400 comprises a first support 206 disposed towards a proximal end 128 of the medicament delivery device 100. The first support 206 is fixedly attached to the main body 102 of the medicament delivery device 100 and comprises the first attraction component 202.

The second attraction component 203 is coupled to a proximal end of the needle cover 118 disposed internally of the main body 102 of the medicament delivery device 100. FIGS. 7A and 7B show the movement of the second attraction component 203 towards the first attraction component 202, as the needle cover 118 is retracted into the main body 102, from the extended position to the retracted position. Movement of the needle cover from the extended position to the retracted position, and the relative movement of the first and second attraction components is described in more detail with reference to FIGS. 2 to 5. The direction of movement of the second attraction component 202 is identified by the arrow 230 in FIG. 7A. In the position shown in FIG. 7B, the first attraction component is engaged with the second attraction component 203, to generate the magnetic attraction force to counteract the biasing force 130 of the biasing member 120.

The first attraction component 202 is arranged in a first plane substantially parallel to the central axis 229 of the medicament delivery device 100. The second attraction component 203 is arranged in a second plane, and is axially moveable along a path in the second plane in a proximal direction to engage the first attraction component 202, and in a distal direction to disengage or release from the first attraction component 202. The second plane is substantially parallel to the central axis 229 of the medicament delivery device 100 and substantially parallel to the first plane. The motion of the second attraction component 203 sliding alongside the first attraction component 202 to bring the first attraction component into proximity with the second attraction component can be referred to as a shear motion.

Although not shown, and the description is not repeated herein for brevity, the first support 206 in FIG. 6 may also comprise an adapter 208 and an attachment mechanism 204 as described with reference to FIGS. 2 to 5. In the same manner as described with reference to FIGS. 2 to 5 the attachment mechanism 204 may also act as the first attraction component 202. Many of the features described above with reference to FIGS. 2 to 5 are also applicable to the hold assistance device 400 shown in FIGS. 6 to 8 and the description is not repeated herein for brevity.

Shear motion of the second attraction component 203 relative to the first attraction component 202 allows for easier disengagement of the first attraction component 202 from the second attraction component 203. This reduces the risk of stall or delay of deployment of the needle cover 118 to extend to cover the needle 116 after medicament delivery has been concluded.

Sliding the second attraction component 203 away from the first attraction component 202 and out of polar alignment can dissipate the magnetic field loop more easily, and potentially allow for greater control of the hold force reduction without the added risk of the magnetic attraction force being too high. A magnetic attraction force that is too high is a force having a magnitude that the biasing force 130 of the biasing member 120 is unable to disengage the first attraction component 202 and the second attraction component 203. As the needle cover 118 is moved towards the extended position such that it protrudes from the main body 102, the biasing member 120, which if a control spring, decreases in strength as it extends. Another example of a magnetic attraction force that is too high is when the magnetic attraction between the first attraction component 202 and the second attraction component 203 is able to prevent or stall the needle cover 118 from fully extending to cover the needle, at any position of the needle cover 118 as it extends from the retracted position to the extended position.

FIGS. 9, 10A and 10B show another example of a hold assistance device 500 and a medicament delivery system 300, wherein like reference numerals denote like elements. In the example shown, the second attraction component 203 is configured to slide towards the first attraction component 202, which rotates in the opposite direction along a track 231, to bring the second attraction component 203 into proximity of the first attraction component 202, to increase the magnetic attraction to generate the magnetic attraction force to counteract the biasing force 130 of the biasing member 120.

The hold assistance device 500 comprises a first support 206 disposed towards a proximal end 128 of the medicament delivery device 100. The first support 206 is fixedly attached to the main body 102 of the medicament delivery device 100 and comprises the first attraction component 202.

The second attraction component 203 is coupled to a proximal end of the needle cover 118 disposed internally of the main body 102 of the medicament delivery device 100. The second attraction component 203 is also arranged on an internal surface 233 of the needle cover 118, i.e., on a surface of the needle cover 118 which is closer the central axis 229 of the medicament delivery device 100, than an external face 234, which is closer to the main body 102 than the central axis 229. FIGS. 10A and 10B show the movement of the second attraction component 203 towards the first attraction component 202, as the needle cover 118 is retracted into the main body 102, from the extended position to the retracted position. Movement of the needle cover from the extended position to the retracted position, and the relative movement of the first and second attraction components 202, 203 is described in more detail with reference to FIGS. 2 to 5. In the position shown in FIG. 10B, the first attraction component 202 is engaged with the second attraction component 203, to generate the magnetic attraction force to counteract the biasing force 130 of the biasing member 120.

The first attraction component 202 is rotationally moveable along a first path relative to the needle cover 118, as the needle cover 118 is moved from the extended to the retracted position. The first attraction component 202 is substantially cylindrical and comprises a series of engagement portions 236 around its circumference. The first attraction component 202 may be a toothed or spur gear.

The needle cover 118 comprises a track 231 which comprises a series of receiving portions 237, for receiving the engagement portions 236 of the first attraction component 202. The track 231 is generally straight and extends along a proximal length of the external face 234 of the needle cover 118. The first attraction component 202 is able to rotate along the track 231 as the needle cover 118 is moved from the extended to the retracted position in a direction 232 as shown in FIG. 10A.

The second attraction component 203 is linearly moveable relative to the first attraction component 202 along a second path. The direction of movement of the second attraction component 202 is identified by the arrow 230 in FIG. 10A. The first path of the first attraction component 202 is substantially parallel to the second path of the second attraction component 203, such that the first attraction component 202 is configured to rotate into engagement with the second attraction component 203 as the needle cover 118 is moved from the extended to the retracted position.

The main body 102 comprises an aperture (not shown) such that the first attraction component 202 is able to engage with the track 231.

Although not shown, and the description is not repeated herein for brevity, the first support 206 in FIG. 9 may also comprise an adapter 208 and an attachment mechanism 204 as described with reference to FIGS. 2 to 5. Many of the features described above with reference to FIGS. 2 to 5 are also applicable to the hold assistance device 500 shown in FIGS. 9, 10A and 10B and the description is not repeated herein for brevity.

The motion of the second attraction component 203 relative to the first attraction component 202 shown and described with reference to FIGS. 9, 10A and 10B can also be referred to as shear motion and therefore the advantages described with reference to FIGS. 6 to 8 to reduce the risk of stall or delay of deployment of the needle cover 118 also apply to the example of FIGS. 9, 10A and 10B.

It can be envisaged that the hold assistance device 200 of FIGS. 2 to 5 can comprise a first attraction component 202 and second attraction component 203 that slide towards one another like that shown in FIGS. 6 to 8, or rotate towards each other like that shown in FIGS. 9, 10A and 10B.

Figure 11:
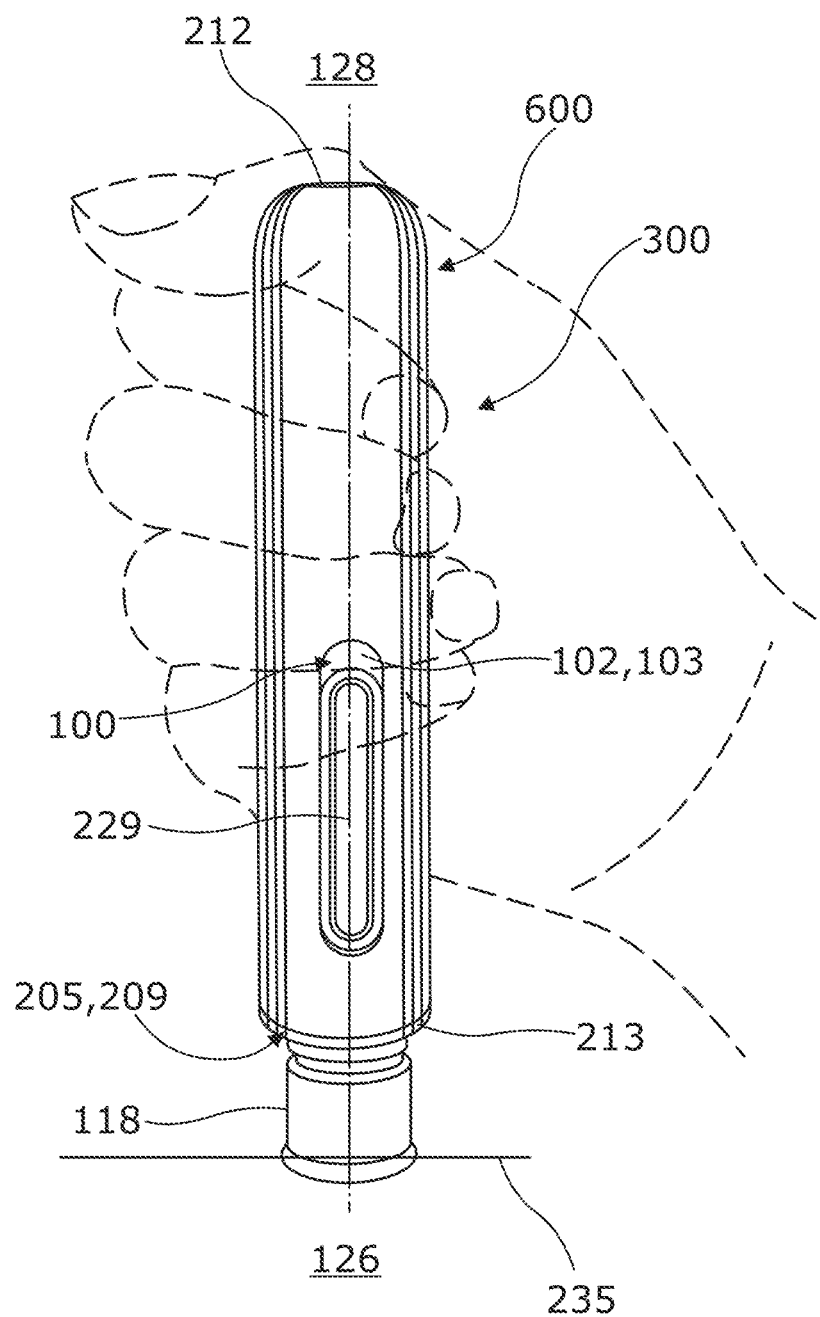
FIG. 11 shows a schematic view of a medicament delivery system including a hold assistance device disposed over a majority of a medicament delivery device.

FIG. 11 shows another example of a hold assistance device 600 and a medicament delivery system 300, wherein like reference numerals denote like elements. In the example shown, the first support 206 comprising the first attraction element 202 extends over a majority of the main body 102 of the medicament delivery device 100 and the second attraction element 203 is coupled to the needle cover 118 disposed within the main body 102. The first support 206 can also be said to extend towards a proximal end of the medicament delivery device 100 and towards a distal end of the medicament delivery device 100.

In some embodiments, the medicament delivery system 300 comprises a combination of the hold assistance device 200 as shown in FIGS. 2 to 6, the hold assistance device 400 as shown in FIGS. 6 to 8, and/or the hold assistance device 500 as shown in FIGS. 9, 10A and 10B, such that during activation of the medicament delivery device 100, two different sets of first attraction components 202 are engaged with two different sets of second attraction components 203. The term different here does not necessarily mean different types, although it can, but that there is more than one set of first attraction component 202 and second attraction component 203. These can be arranged within a first support 206 such as that shown in FIG. 11.

Figure 12:
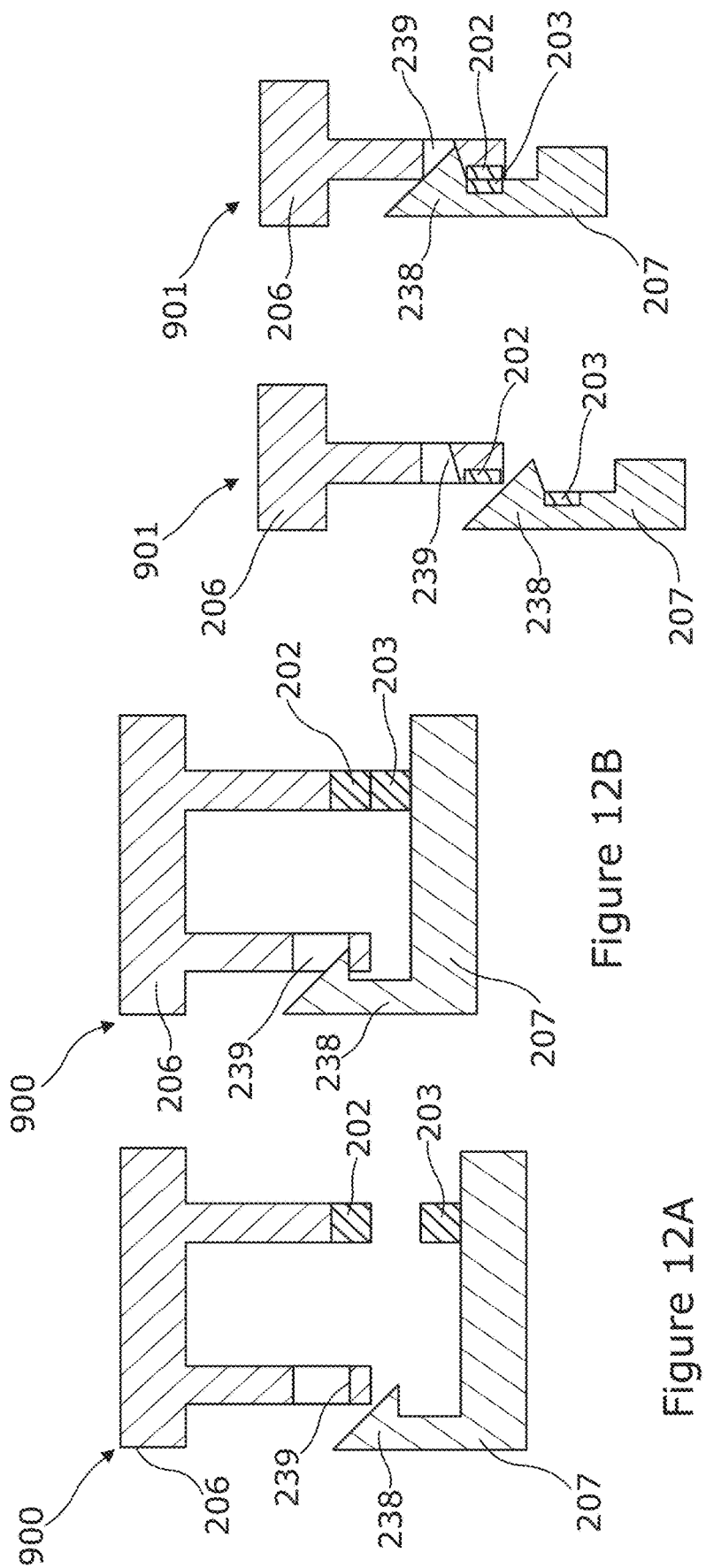
FIG. 12A shows a schematic view of a portion of a hold assistance device comprising a secondary hold component in a rest position.
FIG. 12B shows a schematic view of a portion of a hold assistance device comprising the secondary hold component of FIG. 12A in an actuated position.
FIG. 12C shows a schematic view of a portion of a hold assistance device comprising an alternative secondary hold component in a rest position.
FIG. 12D shows a schematic view of a portion of a hold assistance device comprising the alternative secondary hold component of FIG. 12C in an actuated position.

In any of the above-described embodiments the hold assistance device 200, 400, 500, 600 may comprise a further mechanical advantage (as shown in FIGS. 12A and 12B) such that smaller magnets, or magnets of a lower strength, may be used. The addition of a further mechanical advantage would also provide more design flexibility in how much force is reduced by the magnetic attraction force of the first attraction component 202 and the second attraction component 203.

FIGS. 12A and 12B show an example of a mechanical advantage as described above, wherein the hold assistance device 200, 400, 500, 600 comprises a secondary hold component 238. The secondary hold component 238 can be a mechanical means of reducing the hold force, one example of which is a flexible snap arm. The flexible snap arm 238 is configured to be moveable between a rest position (shown in FIG. 12A) and an actuated position (shown in FIG. 12B). In the example shown, the hold assistance device 900 comprises a second attraction component 203 which is moved axially in a proximal direction towards a first attraction component 202 to generate a magnetic attraction force, similar to the example shown and described with reference to FIGS. 2 to 6. However, it is envisaged that the secondary hold component 238 may be applied to any of the above-described hold assistance devices. The secondary hold component 238 (hereinafter referred to as a snap arm for brevity) is configured to be disengaged from the first support 206 in the rest position, and engaged with a secondary hold slot 239 in the first support 206 in the activated position. The secondary hold slot 239 may be a slot, aperture, notch, chamfer or step. The snap arm 238 is biased into the position shown in FIG. 12B, such that absent any other load, the snap arm 238 engages the first support 206. The snap arm 238 is configured to have a flexibility such that under the biasing force 130 of the biasing member 120, and absent the first and second attraction components 202, 203, the snap arm 238 is unable to remain engaged to the first support 206, and is deflected away from a central axis of the hold assistance device 900. However, when the first attraction component 202 and the second attraction component 203 are engaged to generate the magnetic attraction force, the snap arm 238 is able to remain engaged with the first support 206 until such a time that the magnetic attraction force of the first attraction component 202, and the second attraction component 203, is released. More details of how the magnetic attraction force is released is described above with reference to the other examples. When the snap arm 238 is engaged with the first support 206 it is able to assist the magnetic attraction force in reducing the hold force. Therefore, smaller and/or weaker magnets may be used as the first attraction component 202 and/or the second attraction component 203. It can be envisaged that the snap arm 238 may engage a component of the medicament delivery device 100 or hold assistance device 200, 400, 500, 600, other than the first support 206.

FIGS. 12C and 12D show an example of a hold assistance device 901 comprising an alternative configuration for a secondary hold component 238 (hereinafter referred to as a snap arm for brevity). The snap arm 238 is configured to be moveable between a rest position (shown in FIG. 12C) and an actuated position (shown in FIG. 12D). In the example shown in FIGS. 12C and 12D, the second attraction component 203 is moved axially in a proximal direction towards a first attraction component 202 such that it slides alongside the first attraction component 202 to generate the magnetic attraction force. This is similar to the shear motion described with reference to FIGS. 9, 10A and 10B. However, it is envisaged that the snap arm 238 may be applied to any of the above-described hold assistance devices. For example, the hold assistance device in FIGS. 2 to 6, may comprise a first attraction component 202 and second attraction component 203 which engage by shear motion as described in FIGS. 9, 10A and 10B. The magnetic attraction force is radial, and the first and second attraction components 202, 203 are arranged in a coaxial configuration. The snap arm 238 is configured to be disengaged from the first support 206 in the rest position, and engaged with a secondary hold slot 239 in the first support 206 in the activated position. In the example shown and described in FIGS. 12C and 12D the second attraction component 203 is located on the snap arms 238. The remaining features of the alternative snap arm 238 are similar to those described with reference to FIGS. 12A and 12B and are not repeated for brevity. By adjusting the magnetic attraction and the angle of the contacting surfaces 240 on the snap arms 238, the sum axial force can be further controlled.

In any of the above-described examples, the first attraction component 202 and/or the second attraction component 203 can be a permanent or a programmable magnet. The use of single, multi-pole or programmable magnet can be used to tailor the attractive force of the first attraction component 202 and/or the second attraction component 203 and tailor how the magnetic attraction force is released using shear, pull or rotation of the first attraction component 202 and the second attraction component 203. Using programmable magnets patterned in specific patterns can create a peak attraction when the first attraction component 202 and the second attraction component 203 are slightly separated, and can offer greater control of the attraction with varying axial position, resulting in less sensitivity to geometric tolerances.

There are many advantages provided by the examples shown and described above, including those already mentioned. However, in addition to the above, the hold assistance device, and the medicament delivery system allow for a relatively large force reduction without introducing a large number of moving parts. The force reduction from magnets is very localised and is greatest at the end of the needle cover stroke when the spring force is high, which means there is a low risk of stall when the needle cover 118 is moving from the retracted position to the extended position. Stall of the needle cover 118 moving from the retracted position to the extended position may increase the risk of a user experiencing needle sticks or injury due to the needle cover 118 not covering the needle 116 as quickly after medicament delivery has concluded. As the hold assistance device 200 is removable and in most examples an entirely separate component, it can function with the caps of existing medicament delivery devices as the hold assistance device 200 can be applied after removal of the medicament delivery device cap 110. The hold assistance device has minimal or no influence on the inserted needle depth which can impact on the pharmacokinetic profile of the injected medicament. The hold assistance device has minimal or no influence on the activation force required to operate the device. Finally, the hold assistance device mostly does not require modifications to the main body 102 of existing medicament delivery devices.

Figure 13:
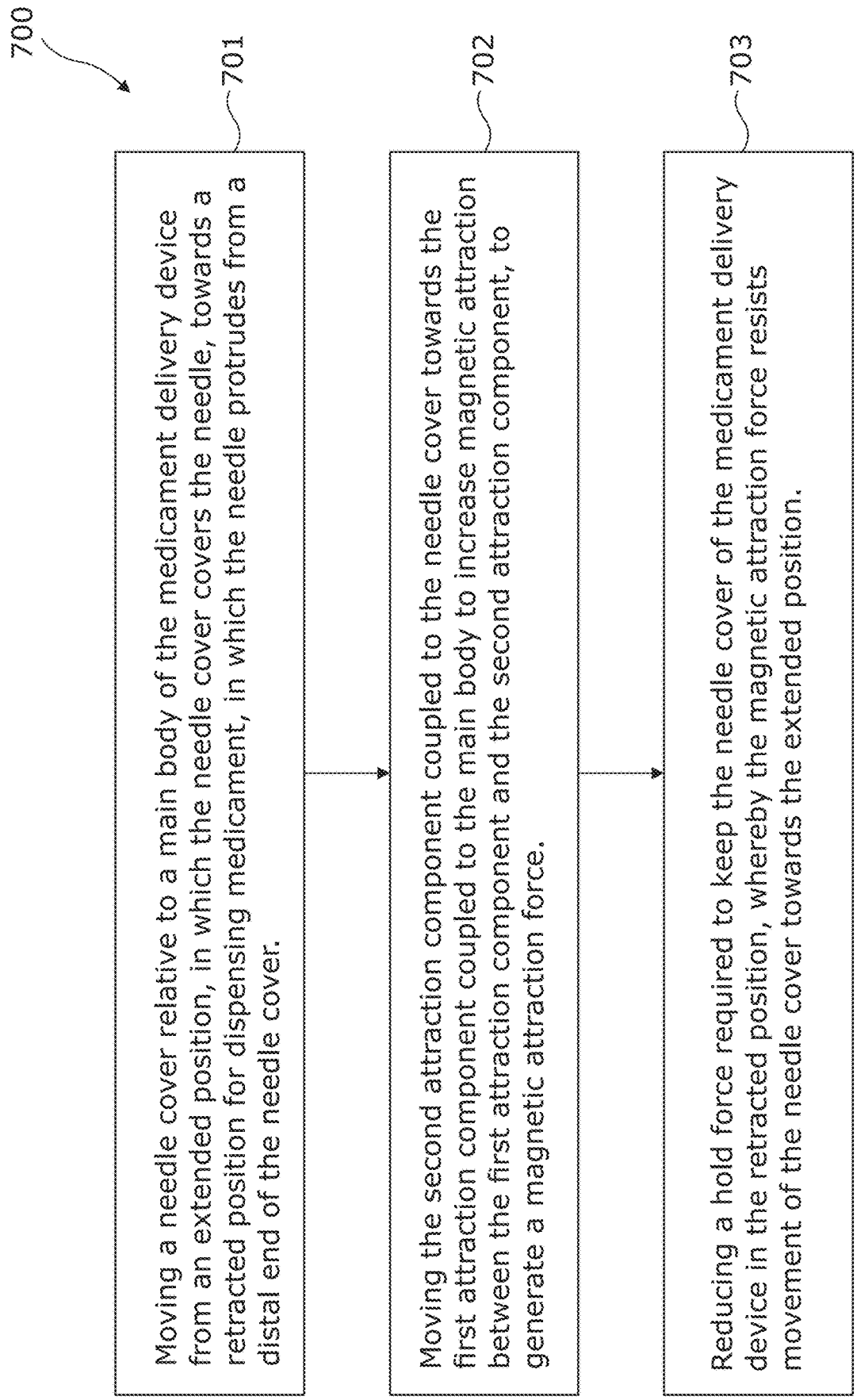
FIG. 13 shows a flowchart of the method steps of a method of operating a medicament delivery system.

FIG. 13 shows a flowchart depicting an example method 700 of operating a medicament delivery system, for example medicament delivery systems 300 as described above.

In step 701, the needle cover 118 is moved relative to the main body 102 from the extended position, in which the needle cover 118 covers the needle 116, to the retracted position, such that, for example, the needle cover 118 is retracted inside the main body 102 such that the needle 116 is exposed, i.e. the needle 116 protrudes from a distal end of the needle cover, to place the medicament delivery device 100 in a state ready for medicament to be delivered from the needle 116 to an injection site 235 of a patient.

The needle cover 118 may be moved from the extended position to the retracted position for example by placing the medicament delivery device 100 against the skin of a patient at an injection site 235, and applying a force in the distal direction, i.e. in a direction towards the injection site 235, thus pushing the needle cover 118, or the blocking member 225, against the skin and causing the needle cover 118 to be pushed inside the main body 102.

In step 702, the second attraction component 203 coupled to the needle cover 118 is moved towards the first attraction component 202 coupled to the main body 102 to increase magnetic attraction between the first attraction component 202 and the second attraction component 203, to generate a magnetic attraction force. Step 702 may occur simultaneously with step 701. In other words, it may be the occurrence of step 701 that may cause step 702 to happen.

In step 703, the hold force required to keep the needle cover 118 of the medicament delivery device 100 in the retracted position is reduced, whereby the magnetic attraction force resists movement of the needle cover 118 towards the extended position.

A user of the medicament delivery system 300 may hold the medicament delivery device 100 for a required duration of time at an injection site 235 of a user. For example, the user may hold the medicament delivery device 100 at the injection site 235 for the amount of time required for completion of delivery of a medicament from the needle 116 to be complete.

Holding the medicament delivery device for a required duration of time at an injection site of a patient may occur after the step of moving the second attraction component 203 coupled to the needle cover 118 towards the first attraction component 202 coupled to the main body 102 to increase magnetic attraction between the first attraction component 202 and the second attraction component 203, to generate a magnetic attraction force.

The magnetic attraction force acting on the needle cover 118 may be released by removing the medicament delivery system 300 from the injection site 235, such that the needle cover 118 moves towards its extended position and the second attraction component 203 is moved out of engagement with the first attraction component 202, separating the first attraction component 202 and the second attraction component 203.

The magnetic attraction force acting on the needle cover may be released by moving the medicament delivery device away from a surface, for example away from the skin of a patient at an injection site.

The needle cover 118 may be moved from the retracted position back into the extended position, such that the needle 116 is covered, which may be desirable for reasons of safety and hygiene. The needle cover 118 may be moved from the retracted position back into the extended position by, for example, removing a user hold force acting on the medicament delivery device 100, for example by moving the medicament delivery device 100 away from an injection site 235 of a patient. For example, by moving the medicament delivery device 100 in the proximal direction away from the skin of a user, this may remove the user hold force pushing the needle cover 118 inside the main body 102 as a result of pressing the needle cover 118 against the skin, such that when the medicament delivery device 100 is moved away, the needle cover 118 is permitted to extend outwards again under the action of the biasing force 130 of the needle cover biasing member 120, which is no longer offset by the magnetic attraction force, since the first attraction component 202 and the second attraction component 203 have been disengaged.

Figure 14:
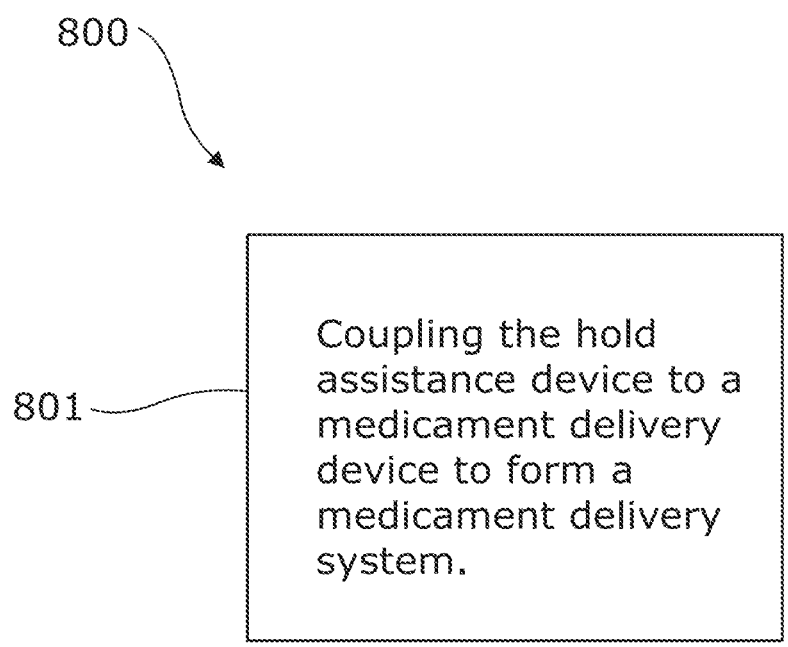
FIG. 14 shows a flowchart of the method steps of a method of assembling a medicament delivery system.

FIG. 14 shows a flowchart depicting an example method 800 of assembling a medicament delivery system. The method 800 of FIG. 13 comprises a step 801 of coupling the hold assistance device 200, 400, 500, 600 to a medicament delivery device 100 to form a medicament delivery system 300.

In all the above-described examples, the attractive force of the first attraction component 202 and the second attraction component 203 (referred to as the magnetic attraction force) is opposite to the expansive force 130 of the needle cover biasing member 120 during drug delivery, resulting in a reduction of the hold force required from the user.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about-4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g., a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly (A21), Arg (B31), Arg (B32) human insulin (insulin glargine); Lys (B3), Glu (B29) human insulin (insulin glulisine); Lys (B28), Pro (B29) human insulin (insulin lispro); Asp (B28) human insulin (insulin aspart); human insulin, wherein proline in position B28 is replaced by Asp, Lys, Leu, Val or Ala and wherein in position B29 Lys may be replaced by Pro; Ala (B26) human insulin; Des (B28-B30) human insulin; Des (B27) human insulin and Des (B30) human insulin.

Examples of insulin derivatives are, for example, B29-N-myristoyl-des (B30) human insulin, Lys (B29) (N-tetra-decanoyl)-des (B30) human insulin (insulin detemir, Levemir®); B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-gamma-glutamyl)-des (B30) human insulin, B29-N-omega-carboxypentadecanoyl-gamma-L-glutamyl-des (B30) human insulin (insulin degludec, Tresiba®); B29-N-(N-lithocholyl-gamma-glutamyl)-des (B30) human insulin; B29-N-(ω-carboxyheptadecanoyl)-des (B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C (Efpeglenatide), HM-15211, CM-3, GLP-1 Eligen, ORMD-0901, NN-9423, NN-9709, NN-9924, NN-9926, NN-9927, Nodexen, Viador-GLP-1, CVX-096, ZYOG-1, ZYD-1, GSK-2374697, DA-3091 MAR-701, MAR709, ZP-2929, ZP-3022, ZP-DI-70, TT-401 (Pegapamodtide), BHM-034. MOD-6030, CAM-2036, DA-15864, ARI-2651, ARI-2255, Tirzepatide (LY3298176), Bamadutide (SAR425899), Exenatide-XTEN and Glucagon-Xten.

An example of an oligonucleotide is, for example: mipomersen sodium (Kynamro®), a cholesterol-reducing antisense therapeutic for the treatment of familial hypercholesterolemia or RG012 for the treatment of Alport syndrome.

Examples of DPP4 inhibitors are Linagliptin, Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present invention include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present invention, which encompass such modifications and any and all equivalents thereof.

An example drug delivery device may involve a needle-based injection system as described in Table 1 of section 5.2 of ISO 11608-1: 2014 (E). As described in ISO 11608-1: 2014 (E), needle-based injection systems may be broadly distinguished into multi-dose container systems and single-dose (with partial or full evacuation) container systems. The container may be a replaceable container or an integrated non-replaceable container.

As further described in ISO 11608-1: 2014 (E), a multi-dose container system may involve a needle-based injection device with a replaceable container. In such a system, each container holds multiple doses, the size of which may be fixed or variable (pre-set by the user). Another multi-dose container system may involve a needle-based injection device with an integrated non-replaceable container. In such a system, each container holds multiple doses, the size of which may be fixed or variable (pre-set by the user).

As further described in ISO 11608-1: 2014 (E), a single-dose container system may involve a needle-based injection device with a replaceable container. In one example for such a system, each container holds a single dose, whereby the entire deliverable volume is expelled (full evacuation). In a further example, each container holds a single dose, whereby a portion of the deliverable volume is expelled (partial evacuation). As also described in ISO 11608-1: 2014 (E), a single-dose container system may involve a needle-based injection device with an integrated non-replaceable container. In one example for such a system, each container holds a single dose, whereby the entire deliverable volume is expelled (full evacuation). In a further example, each container holds a single dose, whereby a portion of the deliverable volume is expelled (partial evacuation).

Those of skill in the art will understand that modifications (additions and/or removals) of various components of the embodiments described herein may be made without departing from the full scope and spirit of the present invention, which encompass such modifications and any and all equivalents thereof.

LIST OF REFERENCE NUMBERS

100—injection device
102—outer casing/housing/main body
103—side wall of main body
104—reservoir
106—plunger
108—collar
110—cap
112—longitudinal axis
113—stopper
114—rear casing
116—needle
118—needle shroud/sleeve/cover
120—control spring/biasing member
122—drive spring
126—distal end
128—proximal end
130—biasing force
200—hold assistance device
202—first attraction component
203—second attraction component
204—attachment mechanism 205—receiving volume of hold assistance device.
206—first support
207—second support
208—adapter
209—first support receiving volume
210—outer housing
211—adapter secondary latch
212—first support proximal end
213—first support distal end
214—axial direction
215—protrusion
216—notch
217—second support proximal end
218—second support distal end
219—outer housing connecting portion
220—receiving portion second support
221—distal cylindrical portion
222—proximal cylindrical portion
223—adapter cavity
224—second support cavity
225—blocking portion
228—needle aperture
229—central axis
230—direction of movement of the second attraction component
231—track
232—direction of rotation of first attraction component
233—internal surface of the needle cover
234—external surface of the needle cover
235—injection site
236—engagement portions
237—receiving portions
238—secondary hold component
239—secondary hold slot
240—contacting surfaces
300—medicament delivery system
400—hold assistance device
500—hold assistance device
600—hold assistance device
700—method
800—method
900—hold assistance device
901—hold assistance device

The invention claimed is:

1. A hold assistance device for use with a medicament delivery device, the hold assistance device comprising:
a first support configured to be fixedly coupled to a main body of the medicament delivery device, wherein the first support comprises a hold slot and a first attraction component coupled to the hold slot; and
a second support, moveable relative to the first support between an initial position and a hold position, and configured to be fixedly coupled to a needle cover of a medicament delivery device, the second support comprising a snap arm and a second attraction component coupled to the snap arm,
wherein at least one of the first attraction component and the second attraction component is a magnet, and the other of the first attraction component and the second attraction component is a magnet or a ferromagnetic material,
wherein movement of the second support towards the hold position moves the second attraction component axially in a proximal direction towards the first attraction component such that the second attraction component slides alongside the first attraction component, increasing magnetic attraction between the first attraction component and the second attraction component to generate a magnetic attraction force, and
wherein when the second support is in the hold position, the magnetic attraction force generated by the first attraction component and the second attraction component is configured to reduce a hold force required to keep the needle cover of the medicament delivery device in a retracted position by resisting movement of-the needle cover towards an extended position, and the snap arm of the second support is configured to engage with the hold slot of the first support to assist the magnetic attraction force in reducing the hold force.

2. The hold assistance device of claim 1, wherein the second support comprises a second cavity for receiving a portion of the first support, when the second support is in the hold position.

3. The hold assistance device of claim 1, wherein the first support comprises a first cavity for receiving a portion of the second support, when the second support is in the hold position.

4. The hold assistance device of claim 1, wherein the second support comprises a blocking portion for engagement with the needle cover of the medicament delivery device, wherein the blocking portion is configured to block movement of the needle cover in a distal direction.

5. The hold assistance device of claim 4, wherein the blocking portion is disposed at a distal most end of the second support and extends at least partially towards a central axis of the hold assistance device, wherein the blocking portion comprises an aperture in a center of the blocking portion to enable a needle to protrude during a medicament delivery.

6. A hold assistance device for use with a medicament delivery device which comprises a main body and a needle cover disposed within the main body and moveable between an extended position and a retracted position, the hold assistance device comprising:
a first support configured to be fixedly coupled to the main body of the medicament delivery device, wherein the first support comprises a hold slot and a first attraction component coupled to the hold slot for engagement with a second attraction component fixedly coupled to a snap arm of the needle cover of the medicament delivery device, wherein the first attraction component is a magnet or a ferromagnetic material,
wherein movement of the needle cover towards the retracted position moves the second attraction component axially in a proximal direction towards the first attraction component such that the second attraction component slides alongside the first attraction component of the hold assistance device, increasing magnetic attraction between the first attraction component and the second attraction component to generate a magnetic attraction force, and
wherein the magnetic attraction force of the hold assistance device is configured to reduce a hold force required to keep the needle cover of the medicament delivery device in the retracted position by resisting movement of the needle cover towards the extended position, and the snap arm of the second support is configured to engage with the hold slot of the first support to assist the magnetic attraction force in reducing the hold force.

7. The hold assistance device of claim 6, wherein the first support comprises a mechanical gripping component for fixedly attaching the hold assistance device to the medicament delivery device.

8. The hold assistance device of claim 7, wherein the first support comprises an adapter configured to house the mechanical gripping component, wherein the first support comprises an outer housing surrounding the adapter, and wherein the adapter is adapted to suit different types of medicament delivery device without changing dimensions of the outer housing.

9. The hold assistance device of claim 7, further comprising a secondary hold component moveable between a rest position, in which the secondary hold component is configured to be disengaged from the first support, and an activated position, in which the secondary hold component is configured to be engaged with the first support, wherein the secondary hold component is configured to be in the activated position when the first attraction component is engaged with a second attraction component to generate the magnetic attraction force, and the secondary hold component is configured to disengage from the activated position, when the magnetic attraction force is released.

10. The hold assistance device of claim 7, wherein the magnet is a programmable magnet.

11. A medicament delivery system comprising a hold assistance device and a medicament delivery device,
wherein the hold assistance device comprises:
a first support configured to be fixedly coupled to a main body of the medicament delivery device, wherein the first support comprises a hold slot and a first attraction component; and
a second support, moveable relative to the first support between an initial position and a hold position, and configured to be fixedly coupled to a needle cover of the medicament delivery device, the second support comprising a snap arm and a second attraction component coupled to the snap arm,
wherein at least one of the first attraction component and the second attraction component is a magnet, and the other of the first attraction component and the second attraction component is a magnet or a ferromagnetic material,
wherein movement of the second support towards the hold position moves the second attraction component axially in a proximal direction towards the first attraction component such that the second attraction component slides alongside the first attraction component, increasing magnetic attraction between the first attraction component and the second attraction component to generate a magnetic attraction force, and
wherein when the second support is in the hold position, the magnetic attraction force generated by the first attraction component and the second attraction component is configured to reduce a hold force required to keep the needle cover of the medicament delivery device in a retracted position by resisting movement of the needle cover towards an extended position, and the snap arm of the second support is engaged with the hold slot of the first support to assist the magnetic attraction force in reducing the hold force,
wherein the medicament delivery device comprises:
a main body arranged to receive a medicament cartridge;
a needle for delivery of medicament from the medicament cartridge; and
the needle cover moveable relative to the main body between the extended position, in which the needle cover covers the needle, and the retracted position for dispensing medicament from the medicament delivery device, wherein in the retracted position the needle protrudes from a distal end of the needle cover,
wherein the first support comprising the first attraction component is configured to be coupled to the main body, and the second attraction component is configured to be coupled to the needle cover.

12. A medicament delivery system of claim 11, further comprising a control spring to bias the needle cover away from the retracted position, wherein the magnetic attraction provided by the first attraction component and the second attraction component counteracts a force of the control spring moving the needle cover away from the retracted position.

13. The medicament delivery system of claim 11, further comprising the medicament cartridge containing a medicament.

* * * * *